US011103991B2

(12) United States Patent
Polygerinos et al.

(10) Patent No.: US 11,103,991 B2
(45) Date of Patent: Aug. 31, 2021

(54) ASSISTED LIFTING DEVICES

(71) Applicants: Panagiotis Polygerinos, Gilbert, AZ (US); Carly Thalman, Mesa, AZ (US); Quoc Lam, Glendale, AZ (US)

(72) Inventors: Panagiotis Polygerinos, Gilbert, AZ (US); Carly Thalman, Mesa, AZ (US); Quoc Lam, Glendale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 77 days.

(21) Appl. No.: 16/486,072

(22) PCT Filed: Mar. 21, 2019

(86) PCT No.: PCT/US2019/023436
§ 371 (c)(1),
(2) Date: Aug. 14, 2019

(87) PCT Pub. No.: WO2019/183397
PCT Pub. Date: Sep. 26, 2019

(65) Prior Publication Data
US 2020/0376650 A1 Dec. 3, 2020

Related U.S. Application Data

(60) Provisional application No. 62/646,264, filed on Mar. 21, 2018.

(51) Int. Cl.
*B25J 9/00* (2006.01)
*B25J 9/14* (2006.01)
*A61F 5/01* (2006.01)

(52) U.S. Cl.
CPC ............. *B25J 9/0006* (2013.01); *A61F 5/013* (2013.01); *B25J 9/142* (2013.01); *A61F 2005/0155* (2013.01)

(58) Field of Classification Search
CPC .. B25J 9/0006; B25J 9/142; A61F 2005/0155; A61F 5/013
See application file for complete search history.

(56) References Cited

U.S. PATENT DOCUMENTS 5,514,081 A * 5/1996 Mann ..................... A61F 5/0118
602/20
7,476,102 B2 * 1/2009 Maples .................... A61F 5/013
434/247

(Continued)

FOREIGN PATENT DOCUMENTS

FR 3070617 A1 * 3/2019 ............. F15B 15/10
WO 2018/136004 A1 7/2018

(Continued)

OTHER PUBLICATIONS

Al-fahaam et al., The design and mathematical modelling of novel extensor bending pneumatic artificial muscles (EBPAMs) for soft exoskeletons. Robotics and Autonomous Systems, 99:44084, 2017.

(Continued)

*Primary Examiner* — Khoi H Tran
*Assistant Examiner* — Rodney P King
(74) *Attorney, Agent, or Firm* — Michael Best & Friedrich LLP

(57) ABSTRACT

An assisted lifting device includes an adjustable sleeve configured to be worn on an arm of a subject and an array of inflatable actuators connected to the adjustable sleeve. Each of the actuators defines an axis. The axes of the two outermost actuators in the array are each configured to be oriented perpendicular to the arm of the subject. The assisted lifting device also includes a retainer coupled to the sleeve and one of the outermost actuators to maintain the perpendicular orientation of the outermost actuator upon inflation of the plurality of actuators.

8 Claims, 15 Drawing Sheets

(56) References Cited

U.S. PATENT DOCUMENTS

| | | | |
|---|---|---|---|
| 9,446,735 B1* | 9/2016 | Jayasuriya | B60R 21/232 |
| 10,265,857 B2* | 4/2019 | Sankai | B25J 17/00 |
| 10,611,020 B2* | 4/2020 | Griffith | A61H 1/024 |
| 10,780,012 B2* | 9/2020 | Lamb | A61H 3/00 |
| 10,860,014 B2* | 12/2020 | Floreano | A63H 30/04 |
| 2014/0318118 A1* | 10/2014 | Mazzeo | F03G 7/06 60/527 |
| 2015/0173993 A1 | 6/2015 | Walsh et al. | |
| 2015/0266186 A1 | 9/2015 | Mosadegh et al. | |
| 2015/0290794 A1 | 10/2015 | Griffith et al. | |
| 2016/0136820 A1 | 5/2016 | Lessing et al. | |
| 2016/0278948 A1 | 9/2016 | Piercy et al. | |
| 2017/0119614 A1* | 5/2017 | Yeow | A61H 1/0285 |
| 2018/0079071 A1 | 3/2018 | Griffith et al. | |
| 2018/0289522 A1 | 10/2018 | Zhu et al. | |
| 2018/0296425 A1* | 10/2018 | Lamb | B25J 9/0006 |
| 2019/0029914 A1 | 1/2019 | Polygerinos et al. | |
| 2019/0167504 A1 | 6/2019 | Polygerinos et al. | |
| 2019/0247217 A1 | 8/2019 | Govin et al. | |
| 2019/0314980 A1 | 10/2019 | Polygerinos et al. | |
| 2019/0336315 A1 | 11/2019 | Polygerinos et al. | |

FOREIGN PATENT DOCUMENTS

| | | | |
|---|---|---|---|
| WO | 2018136004 A1 | 7/2018 | |
| WO | 2018/222930 A1 | 12/2018 | |
| WO | 2018222930 A1 | 12/2018 | |
| WO | 2019183397 A1 | 9/2019 | |

OTHER PUBLICATIONS

Author Not Available, Standards for reporting emg data. Journal of Electromyography and Kinesiology, 38:I-II, 2018. Neuromechanics of fine hand-motor tasks.

Bureau of Labor Statistics. Employer-Reported Workplace Injuries and Illnesses. Technical Report USDL-17-1482, 2017.

Bureau of Labor Statistics. Nonfatal occupational injuries and illnesses requiring days away from work. Technical Report USDL-16-2130, 2016.

Caldwell et al., "Soft" Exoskeletons for Upper and Lower Body Rehabilitation Design, Control and Testing. International Journal of Humanoid Robotics, 04(03):549-573, 2007.

Chen et al., A Lobster-inspired Robotic Glove for Hand Rehabilitation. IEEE International Conference on Robotics and Automation (ICRA), pp. 4782-4787, 2017.

Ding et al., Biomechanical and Physiological Evaluation of Multi joint Assistance with Soft Exosuits. IEEE Transactions on Neural Systems and Rehabilitation Engineering, 25(2):119-130, 2017.

Dinh et al., Hierarchical Cascade Controller for Assistance Modulation in a Soft Wearable Arm Exoskeleton. IEEE Robotics and Automation Letters, 2(3):1786-1793, 2017.

Gopura et al., Developments in hardware systems of active upper-limb exoskeleton robots: A review. Robotics and Autonomous Systems, 75:203-220, 2016.

International Search Report and Written Opinion for Application No. PCT/US2019/023436 dated May 31, 2019 (8 pages).

Kazerooni, Exoskeletons for Human Performance Augmentation, pp. 773-793. Springer Berlin Heidelberg, Berlin, Heidelberg, 2008.

Kim et al., Stability Regions for Standing Balance of Biped Humanoid Robots. pp. 4735-4740, 2017.

Koh et al., Design of a Soft Robotic Elbow Sleeve with Passive and Intent-Controlled Actuation. Frontiers in Neuroscience, 11(October):597, 2017.

Leigh, Economic burden of occupational injury and illness in the United States. The Milbank Quarterly, 89(4):728-72, 2011.

Mislinski, Long-Term Trends in Employment by Age Group. Advisor Perspectives, 2017, <https://talkmarkets.com/content/economics--politics/long-term-trends-in-employment-by-age-group?post=141637> (9 pages).

Natividad et al., A hybrid plastic-fabric soft bending actuator with reconfigurable bending profiles. In 2017 IEEE International Conference on Robotics and Automation (ICRA), pp. 6700-6705, May 2017.

Park et al., Design and control of a bio-inspired soft wearable robotic device for ankle-foot rehabilitation. Bioinspiration & biomimetics, 9(1):016007, 2014.

Polygerinos et al., EMG Controlled Soft Robotic Glove for Assistance During Activities of Daily Living. 2015 IEEE International Conference on Rehabilitation Robotics (ICORR), pp. 55-60, Aug. 2015.

Polygerinos et al., Soft Robotics: Review of Fluid-Driven Intrinsically Soft Devices; Manufacturing, Sensing, Control, and Applications in Human-Robot Interaction. Advanced Engineering Materials, 2017,19(12):1700016.

Simpson et al., Exomuscle: An inflatable device for shoulder abduction support. In 2017 IEEE International Conference on Robotics and Automation (ICRA), pp. 6651-6657, May 2017.

Sridar et al., Development of a soft-inflatable exosuit for knee rehabilitation. In 2017 IEEE/RSJ International Conference on Intelligent Robots and Systems (IROS), pp. 3722-3727, Sep. 2017.

Thalman et al., "A Novel Soft Elbow Exosuit to Supplement Bicep Lifting Capacity," IEEE/RSJ International Conference on Intelligent Robots and Systems, 2018, 7 pages.

Viteckova et al., Wearable lower limb robotics: A review. Biocybernetics and Biomedical Engineering, 33(2):96-105, 2013.

Waters et al., Applications manual for the revised niosh lifting equation. 1994.

Xiloyannis et al., Design and preliminary testing of a soft exosuit for assisting elbow movements and hand grasping. Biosystems and Biorobotics, 15:557-561, 2017.

U.S. Appl. No. 15/829,597, filed Dec. 1, 2017.

International Search Report and Written Opinion received in International Application No. PCT/US2019/023436, dated May 31, 2019 (8 pages).

* cited by examiner

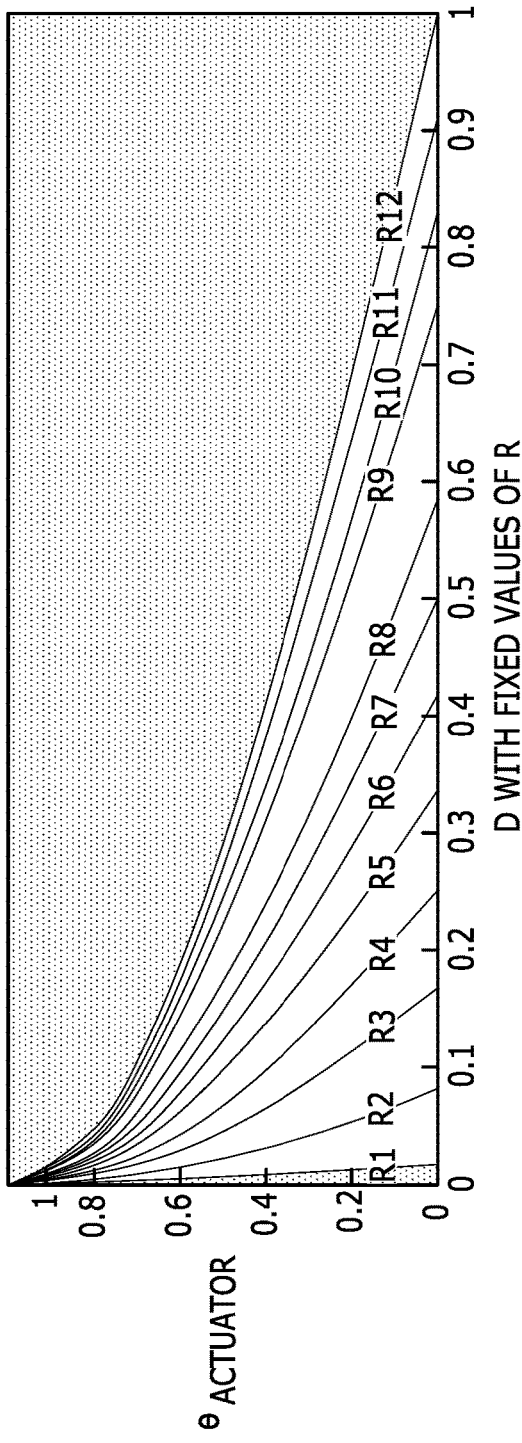
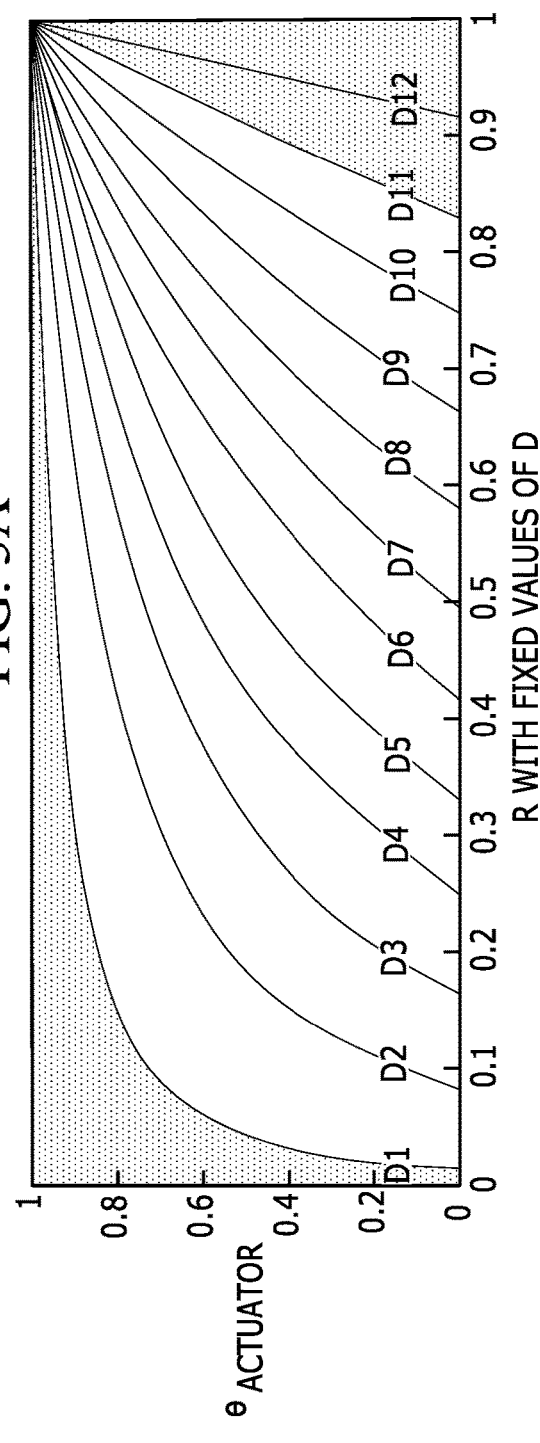

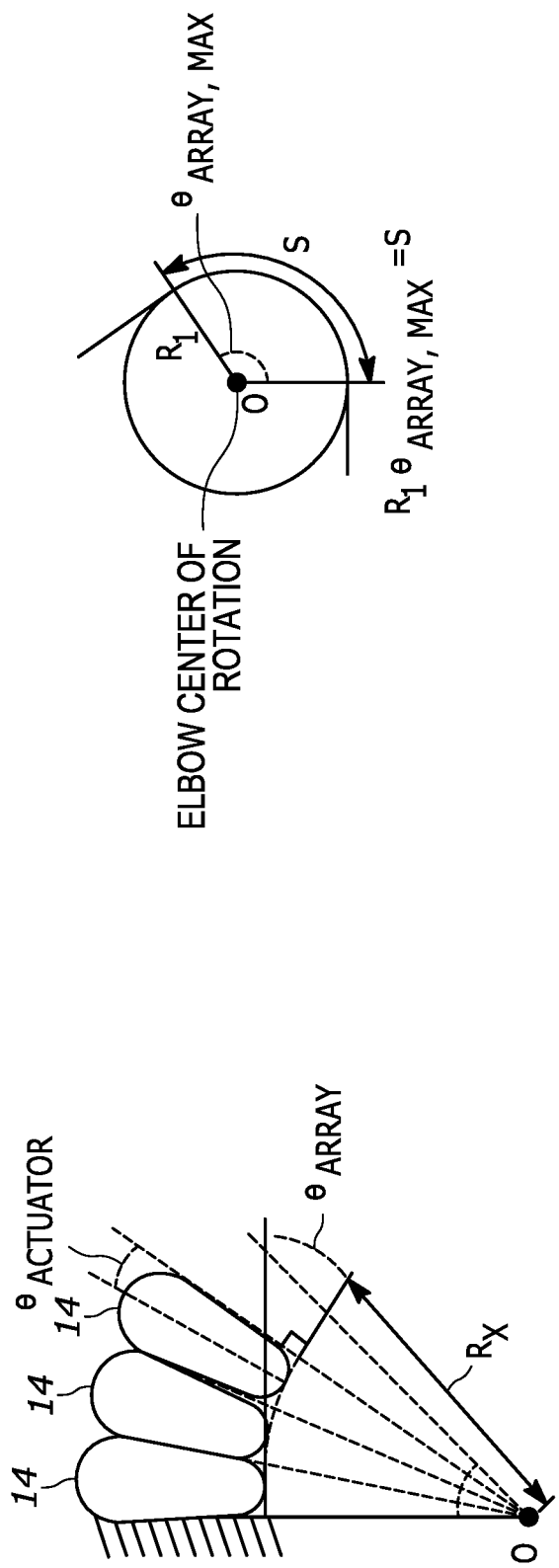
FIG. 6A
FIG. 6B
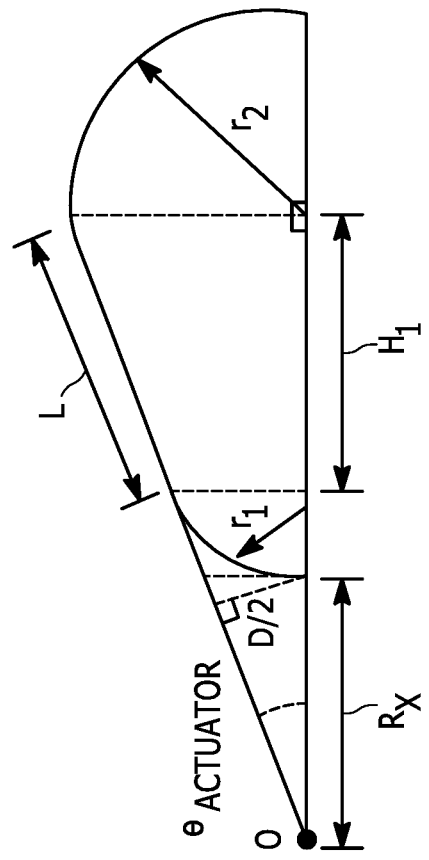
FIG. 6C

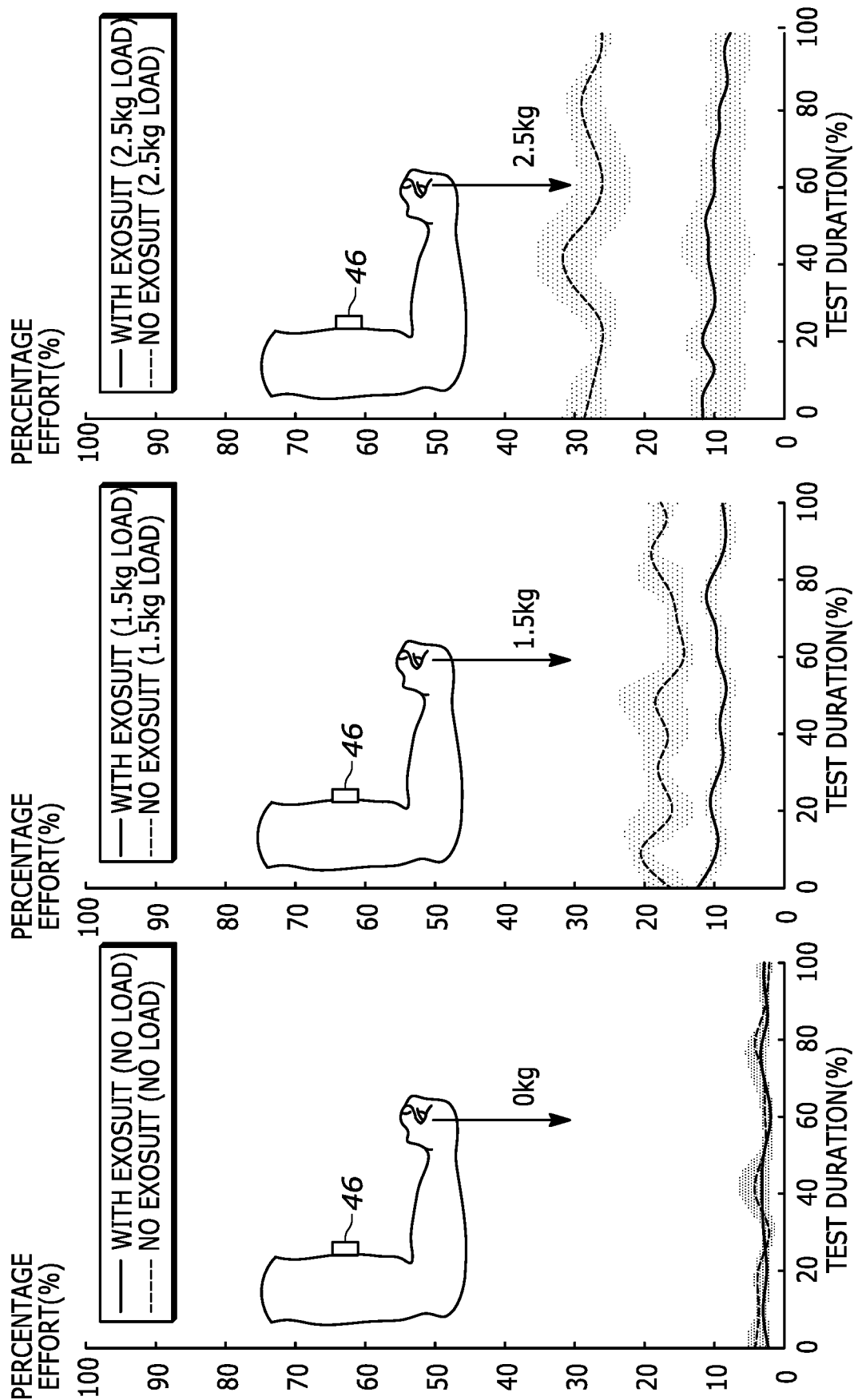

ASSISTED LIFTING DEVICES

CROSS-REFERENCE TO RELATED APPLICATION

This application claims the benefit of U.S. Provisional Patent Application No. 62/646,264, filed Mar. 21, 2018, the entire contents of which are incorporated by reference herein.

BACKGROUND

Freight, stock, and warehouse workers are required to perform strenuous and repetitive tasks such as packing, shelving, loading, and unloading goods on a daily basis. These repetitive motions can lead to muscle fatigue, as well as lower-back and upper-limb injuries that reduce productivity. Injuries in this line of work can cause musculoskeletal disorders (MSDs) as a result of improper lifting postures, repetitive high strain activities, and age-related factors.

Potential solutions for approaching this problem have been seen in the field of wearable robotics. These robotic devices are designed to help augment load carriage capacity and normal muscle function in healthy individuals while reducing the amount of physical exertion the user is required to sustain. Examples of human augmentation via exoskeletons have been seen for multi-purpose use in healthcare, rehabilitation, and industrial settings. There have been a variety of lower-limb exoskeletons and upper-limb devices. These devices seek to increase the load bearing capability of the user. However, the primary concerns of using exoskeletons is that they are rigid, they lack portability, there may be alignment complications with the biological joint they are trying to assist, and they may cause discomfort over long periods of use. Additionally, exoskeletons may have high development costs.

SUMMARY

In some embodiments, a soft elbow exosuit is capable of providing supplemental lifting assistance by reducing muscle activity of the bicep muscle. The exosuit improves the efficiency and endurance of workers who are tasked with repetitive lifting. The exosuit includes an array of pneumatically pressurized soft actuators, which are encased in nylon fabric that allows for a high force-to-weight ratio of 211.5 N/g.

In other embodiments, an assisted lifting device has an adjustable sleeve that is worn on an arm of a subject and an array of inflatable actuators connected to the base. Each of the actuators defines an axis. The axes of two outermost actuators in the array are each configured to be oriented perpendicular to the arm of the subject. The assisted lifting device also includes a retainer coupled to the sleeve and one of the outermost actuators to maintain the perpendicular orientation of the outermost actuator upon inflation of the plurality of actuators.

In other embodiments, an assisted lifting device includes a sleeve to be worn around a user's arm proximate an elbow and an array coupled to the sleeve. The array includes a first retainer positioned on a first end of the array and a second retainer positioned on a second end of the array. The array also includes a first actuator and a second actuator. The first actuator includes a first base to extend at least partially around the user's arm. The first actuator is positioned between the first retainer and the second retainer. The second actuator includes a second base to extend at least partially around the user's arm. The second actuator is spaced apart from the first actuator and is positioned between the first retainer and the second retainer In other embodiments, an assisted lifting device includes a sleeve to be worn on an arm of a subject, a plurality of inflatable actuators coupled to the sleeve, and a first triangular actuator coupled to the sleeve and one of the outermost actuators. Each of the actuators includes a base and a free end. The plurality of actuators are movable between a deflated position and an inflated position. The bases of adjacent actuators are fixed a predetermined distance apart. The free ends of adjacent actuators are spaced further apart than the predetermined distance in the inflated positioned causing the plurality of actuators to curve around the arm of the subject.

Other aspects of the invention will become apparent by consideration of the detailed description and accompanying drawings.

BRIEF DESCRIPTION OF THE DRAWINGS

FIG. 5A illustrates a relationship between $\theta_{actuator}$ and d for incremental values of R normalized from 0° to 90°. The shaded areas are unfeasible regions due to manufacturing constraints.

FIG. 5B illustrates a relationship between $\theta_{actuator}$ and a varying d given a fixed R normalized from 0° to 90°. The shaded areas are unfeasible regions due to manufacturing constraints.

FIG. 6A illustrates an actuator arrangement demonstrating interactions in the array of FIG. 2C.

FIG. 6B illustrates a spherical elbow joint representation of constant radius $R_1$.

FIG. 6C illustrates a section view of an individual actuator of FIG. 6A depicting dimensions used in calculating an interacting area.

FIG. 11C illustrates baseline isometric muscle activity with no load.

FIG. 11D illustrates measured isometric muscle activity of a bicep with a 1.5 kg load.

FIG. 11E illustrates measured muscle activity of the bicep with a 2.5 kg load.

DETAILED DESCRIPTION

Before any embodiments of the invention are explained in detail, it is to be understood that the invention is not limited in its application to the details of construction and the arrangement of components set forth in the following description or illustrated in the following drawings. As those of ordinary skill in the art will readily recognize and appreciate after having studied the teachings set forth in this application, the invention is capable of other embodiments and of being practiced or of being carried out in various ways.

The recent introduction and advancement of soft robotics has led to designs of wearable devices that are safe for human-robot interaction, allow even distribution of force on the user's joints, and are unaffected by alignment issues. These wearable devices are also compliant, lightweight, and have a low cost to fabricate. These intrinsically soft wearable devices may be actuated by cable-driven actuators, pneumatic artificial muscles, fluidic elastomeric actuators, and pneumatically inflatable bladder-based actuators.

Figure 1:
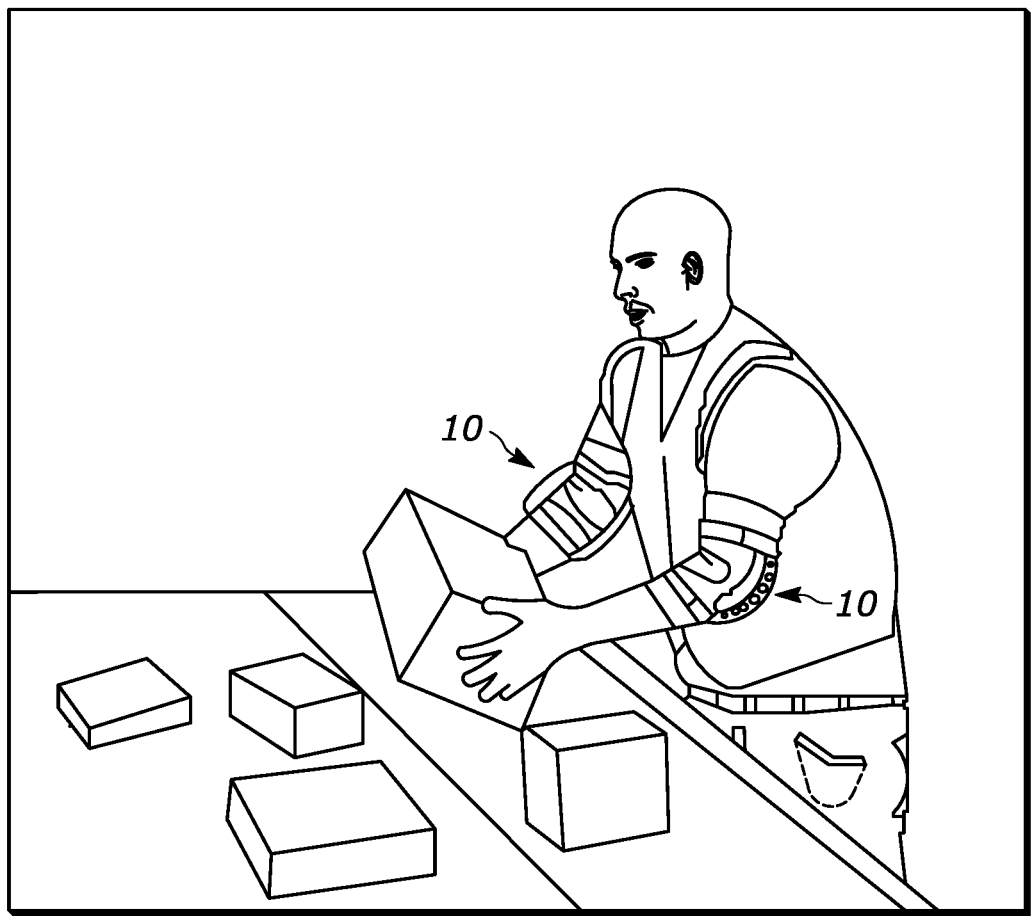
FIG. 1 illustrates a soft robotic elbow exosuit according to one embodiment coupled to a workers elbow in a warehouse environment.

As shown in FIG. 1, an assisted lifting device or soft elbow exosuit 10 is wearable on a user's body. In the illustrated embodiment, the exosuit 10 is positionable on a user's forearm proximate the user's elbow. Additionally, an individual exosuit 10 may be worn on each of the user's forearms proximate each of the user's elbows.

Figure 2A:
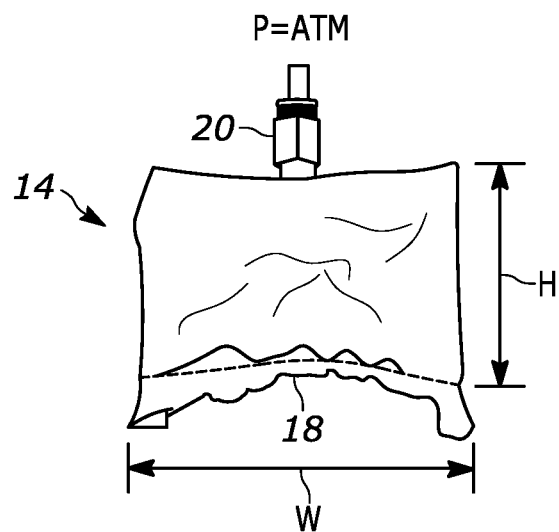
FIG. 2A illustrates a deflated soft actuator of the exosuit of FIG. 1, with labeled dimensions for width, w and height, h.

As shown in FIG. 2A, the soft elbow exosuit 10 includes at least one small, soft cylindrical actuator 14. The actuator 14 may be, for example, formed by hermetically sealing the borders of two sheets of thermoplastic polyurethane (TPU) material. A cavity is formed between the two sheets of TPU material. Each actuator 14 may be also encased in an inextensible fabric (e.g., a weaved nylon material) that has substantially the same net shape as the sheets of TPU material. The inextensible fabric (e.g., nylon material) forms a base 18 of the respective actuator 14. Each actuator 14 includes a height H and a width W, as well as a fluid conduit or tubing 20. The tubing 20 provides fluid communication between an external environment to the actuator 14. This communication allows the internal pressure within the actuator 14 to change.

In the illustrated embodiment, the TPU sheets (e.g., DT-2001, American Polyfilm, Branford, Conn.) are sealed (e.g., using a custom computer numerical control (CNC) router with a modified soldering iron tip) to trace and seal the contours of the soft actuators 14. In some embodiments, a laser cutter (e.g., Glowforge Pro, Glowforge, Seattle, Wash.) is used to cut the outer nylon material pouches into the desired shape. It is then sewn into its final shape with the use of a sewing machine (e.g., SE-400 Brother, Bridgewater, N.J.). In the illustrated embodiment, the height H of the soft actuator 14 has a maximum of 50 mm. This helps to provide a compact, low-profile exosuit 10. Other embodiments include heights H less than 50 mm, or greater than 50 mm. In the illustrated embodiment, the width W of each soft actuator 14 is greater than the height of the respective actuator 14. Other embodiments include an actuator 14 with a width W equal to the height H, or less than the height H.

Figure 2B:
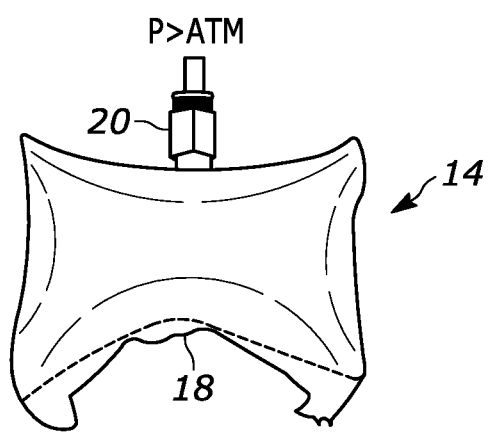
FIG. 2B illustrates the soft actuator of FIG. 2A in an inflated position.

As shown in FIG. 2B, the base 18 bends or curves after the actuator 14 is inflated (i.e., a pressure within the actuator 14 is greater than an atmospheric pressure). The base 18 curves into the body of the actuator 14 (i.e., forming a concave curvature), as the internal pressure increases. The angle of curvature of the actuator 14 may be similar to a curvature of an arm of a human.

Figure 2C:
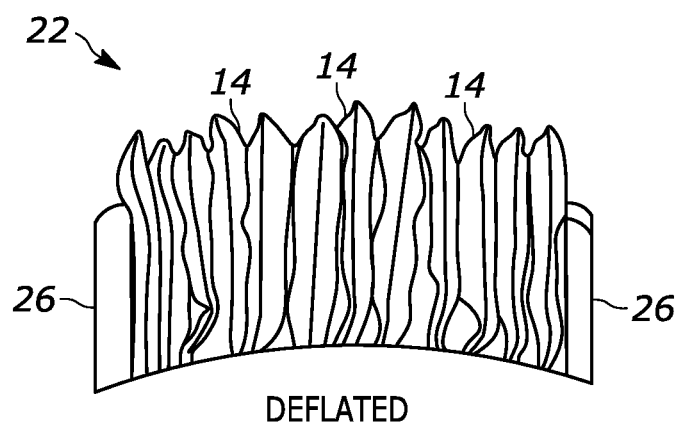
FIG. 2C illustrates an array formed from a plurality of soft actuators of FIG. 2A, in a deflated position.

As shown in FIG. 2C, multiple actuators 14 may be arranged side by side to form an array 22. The array 22 includes two retainers 26. In the illustrated embodiment, the retainers 26 are triangular in shape, and are placed on either side of the array 26. Other embodiments of the retainers 26 include different shapes. The actuators 14 are arranged between each of the retainers 26. In the illustrated embodiment, the minimum distance between the uninflated soft actuators 14 is limited to 5 mm due to manufacturing constraints.

Figure 2D:
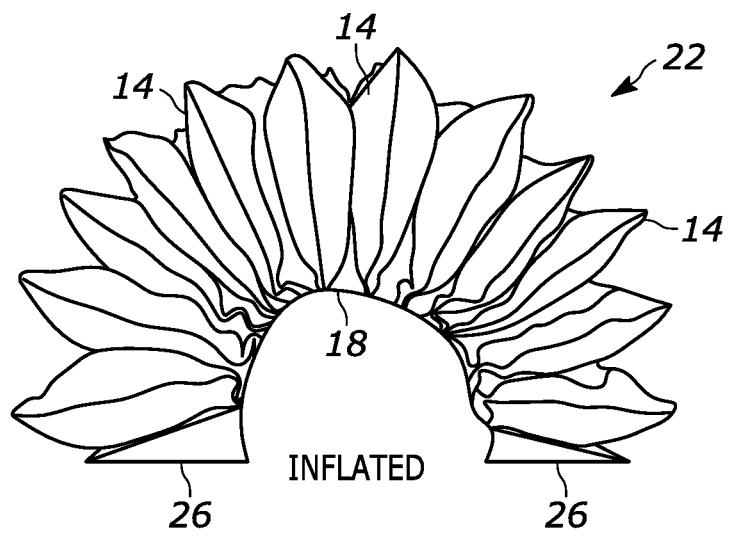
FIG. 2D illustrates the array of FIG. 2C in an inflated state.

As shown in FIG. 2D, when inflated, the individual actuators 14 interact with one another other, to produce a bending motion. As the pressure in the individual actuators 14 increases, the volume of each actuator 14 also increases. Each expanding actuator 14 contacts the adjacent actuators 14. The actuators 14 are coupled in the array 22 along their base 18, and are free opposite the base 18. Thus, there is a fixed spacing d (see e.g., FIGS. 2C and 2D) between the actuators 14 along the bases 18 (e.g., no less than 5 mm). When the actuators 14 expand, this spacing cannot increase (e.g., because the actuators 14 are sewn down). Instead, the actuators 14 are only able to expand on the opposite side from the base 18 (i.e., the free side). The array 22 curves as the individual actuators 14 expand, since the actuators 14 can only move apart on one side.

Arranging the actuators 14 in the array 22 allows the individual actuators 14 to sustain higher pressures than they would be capable of sustaining alone (i.e., as a single actuator 14). The actuators 14 in the array 22 are not limited by the low tensile strength of the TPU during inflation. This allows actuators 14 in the array 22 to obtain higher force-to-weight ratios than from a single actuator 14. The arrangement of the array 22 allows the actuators 14 in the array to obtain a higher force-to-weight ratio than an actuator 14 not part of the array 22 could obtain.

Figure 3A:
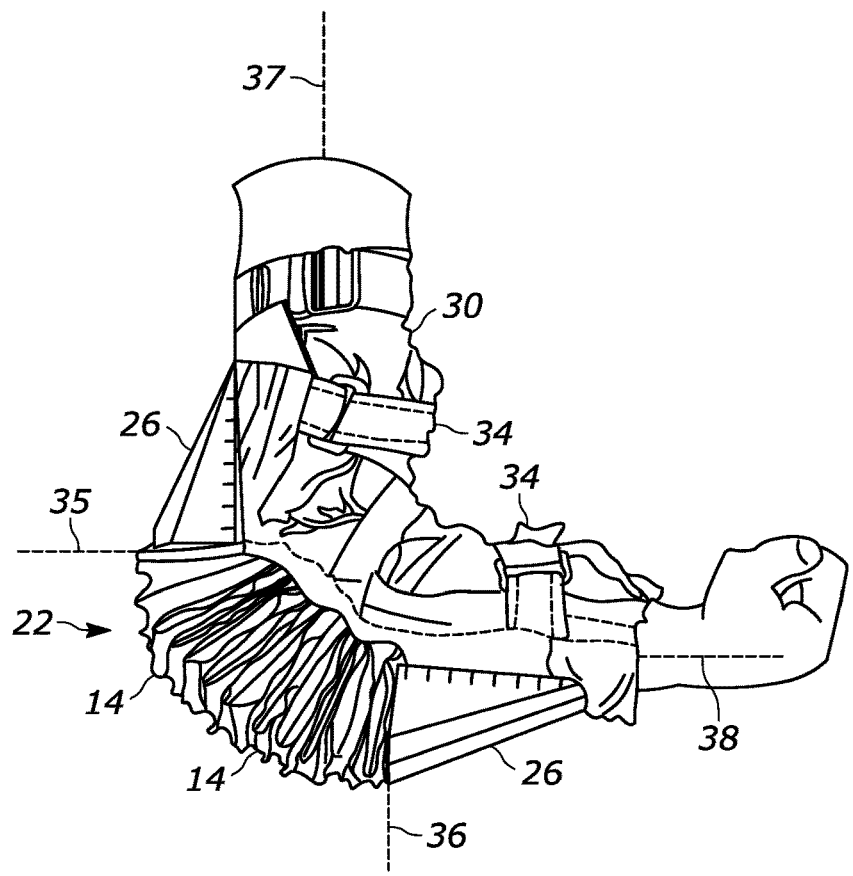
FIG. 3A illustrates an embodiment of the soft robotic elbow exosuit of FIG. 1.

As shown in FIG. 3A, the exosuit 10 includes a sleeve 30 (e.g., a nylon fabric sleeve) that is receivable around a forearm of a user (e.g., around the elbow). The sleeve 30 includes straps 34 and the array 22. The straps 34 are arranged proximate the inner surface of the arm. This allows the user to easily adjust (e.g., tighten or loosen) the straps 34 in order to achieve a desired fit. The straps 34 may be adjustable hook and loop straps 34, and may secure the sleeve 30 to the arm without covering the elbow crease. By adjusting the straps 34, the array 22 is secured against the curvature of the elbow joint so that it does not dislodge from the joint when inflated. The array 22 is positioned on the opposite surface of the sleeve 30 (i.e., proximate the outer surface of the arm).

The bending of the array 22 is constrained to the back of the elbow by the sleeve 30. The soft actuators 14 at the ends of the array 22 are required to remain perpendicular to the arm in order to achieve the maximum torque output. The soft actuator 14 at a first end of the array 22 includes a first actuator axis 35 and the soft actuator 14 at a second end of the array 22 includes a second actuator axis 36. The first actuator axis 35 remains perpendicular to a first arm axis 37 (e.g., an axis along the humerus) and the second actuator axis 36 remains perpendicular to a second arm axis 38 (e.g., an axis along the radius and ulna).

Figure 3B:
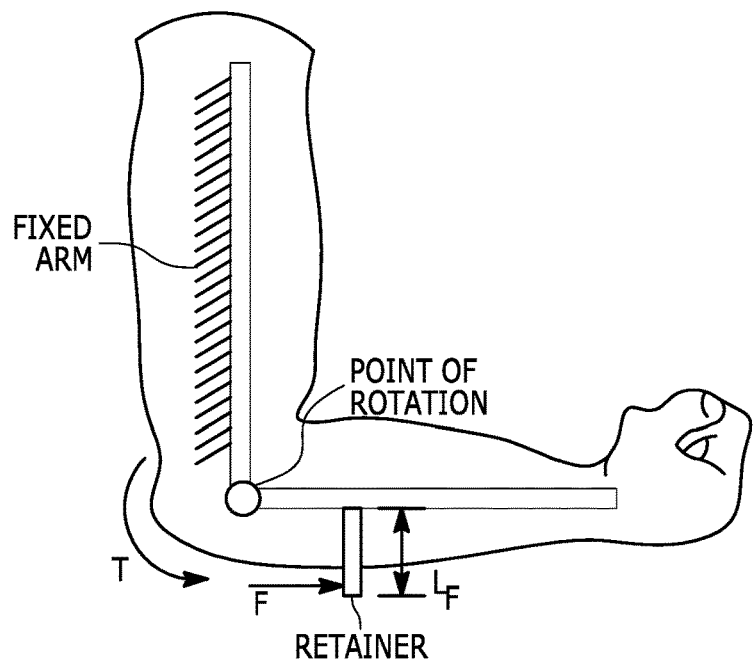
FIG. 3B illustrates a governing free body diagram (FBD) of the actuator array of FIG. 3A against the worker's elbow.

As shown in FIG. 3B, the actuators 14 of the array 22 produce a bending moment given by:

$$T = F \cdot L_F \tag{1}$$

where T is the torque produced about the joint (e.g., the elbow), F is the generated force by pressurization of the array 22 and applied at a height of $L_F$ from the user's elbow (e.g., from the outer surface of the arm to the radius and/or ulna). The force F is determined by the contact area between the soft actuator 14 and retainer 26 (e.g., h·w), and the internal pressure of the actuator 14.

In the illustrated embodiment, the exosuit 10 is designed to provide 30 N·m of torque about the elbow joint to assist the bicep. A lightweight, fabric-based design is implemented through the use of compliant and soft materials. The curvature of each actuator 14 in the array 22 ensures the forces are applied over a distributed area.

Figure 4A:
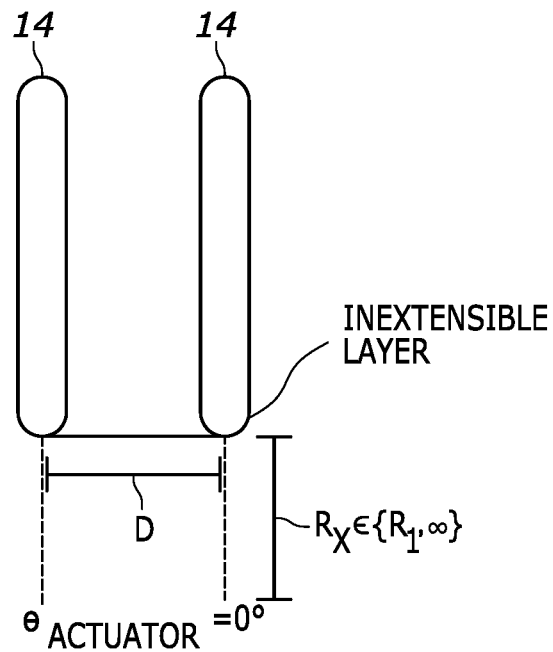
FIG. 4A illustrates a model of two adjacent soft actuators of FIG. 2A in a deflated state, where no contact occurs between the two actuators.
Figure 4B:
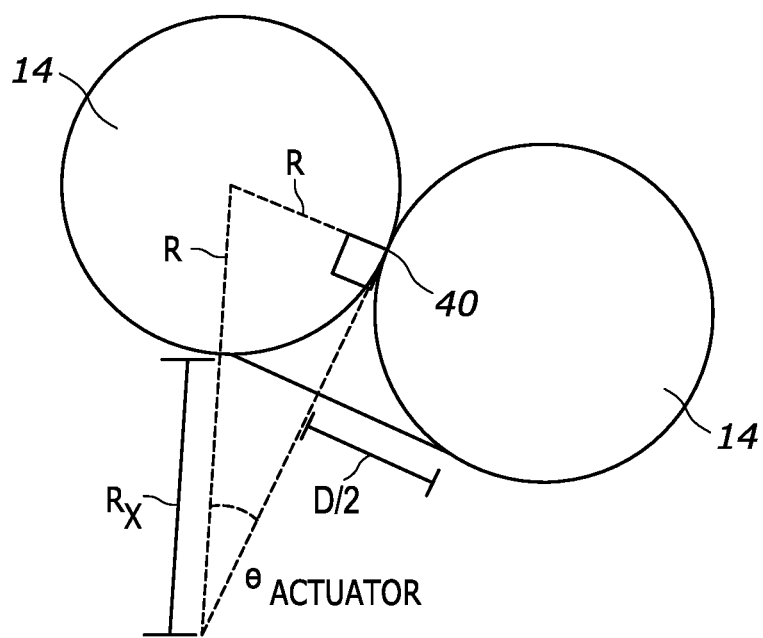
FIG. 4B illustrates a two-dimensional geometric model of the two adjacent soft actuators of FIG. 4A, in a fully pressurized state.

As shown in FIGS. 4A and 4B, a cross-section of two adjacent individual actuators 14 of the array 22 may be simplified to two dimensions in order to model the bending curvature of the array 22. When deflated (see e.g., FIG. 4A), the actuators 14 have no interaction with adjacent actuators 14 in the array 22. Each deflated actuator 14 is spaced apart from adjacent actuators 14 by a distance d. The interaction between two actuators 14 is modeled using the following assumptions: i) the individual actuators 14 inflate to create a circular cross section, ii) the deformation when fully pressurized is negligible, iii) a point contact 40 will form with adjacent actuators 14; and iv) the actuators 14 are fixed at a point to the inextensible layer (see e.g., FIG. 4B). The bending behavior of adjacent actuators 14 is defined as:

$$\theta_{actuator} = \sin^{-1}\left(1 - \frac{d}{2R}\right) \tag{2}$$

where $\theta_{actuator}$ is the bending caused by the interaction of adjacent soft actuators 14, d is the spacing between them, and R is the radius of a single inflated actuator 14. A boundary condition of 2R>d is implemented to ensure that the interaction between two adjacent actuators 14 causes bending for every considered value of $\theta_{actuator}$.

As shown in FIGS. 5A and 5B, the optimal (e.g., maximum) bending angle may be determined by varying one of the R value (FIG. 5A) and d value (FIG. 5B), while the other is set as a constant each time. The $\theta_{actuator}$ increases with both the decrease in d and increase in R. Feasible regions for both R and d are identified by imposing manufacturing constraints depicted by the unshaded regions in FIG. 5.

Possible angles between two actuators 14 have been limited to 90° as the bending angle becomes asymptotic as d becomes infinitely small. The angle $\theta_{actuator}$, represents the angle between the center of an actuator 14 and its edge. It is equivalent to $\theta_{array}/2n$, where $\theta_{array}$ is the elbow angle and n, the number of soft actuators 14 in the array 22.

Modeling the torque output of the array 22 follows the same geometric principles outlined above. However, line contact across two actuators 14 is replaced with the interacting area to account for shape deformation. Additionally, the array 22 is no longer considered in free space bending, but constrained to the elbow joint. The resultant shape of the inflated soft actuators 14 is shown in FIG. 6A.

The total length of the actuator array is represented by:

$$S = R_1 \cdot \theta_{array,max} \tag{3}$$

where, S is the arc length, $R_1$ is the radius of the presumed spherical elbow joint, and $\theta_{array,max}$ is the maximum bending angle of the elbow (see e.g., FIG. 6B). As torque is dependent on the moment arm $L_F$ (see e.g., FIG. 3B), any additional length and/or number of actuators 14 past the retainer 26 has no effect on the torque output.

As a result of the array 22 bending with the elbow, S bends as well with its radius of curvature defined as:

$$R_X(\theta_{array}) = R_1 \frac{\theta_{array,max}}{\theta_{array}} \tag{4}$$

where $R_x$, is the radius of curvature at the current angle, $\theta_{array}$. Equation (4) demonstrates that $R_x$ can range from $R_1$ to $\infty$ (see e.g., FIG. 4A).

As shown in FIG. 6C, the shape of an individual actuator 14 can be approximated as a right triangle with a quarter circle attached to the end. This shape may be used to calculate the reaction force of the actuators of Eq. 1. Using the tangent relationship, the minor radius, $r_1$ is determined to be:

$$r_1(\theta_{actuator}) = \frac{dR_x}{2R_x \cos(\theta_{actuator})}. \tag{5}$$

While the major radius, $r_2$, also utilizes the tangent, the solution is expressed as $$r_2(\theta_{actuator}) = -b + \sqrt{\frac{b^2 - 4ac}{2a}}, \tag{6}$$

where a, b, and c are defined by $$a = 1 + \frac{1}{\left(\pi R + \sqrt{(R_x + r_1)^2 + r_1^2}\right)^2} + \left(\frac{\pi}{2}\right)^2, \tag{7}$$

$$b = \pi^2 R + \pi \sqrt{(R_x + r_1)^2 + r_1^2} - \frac{\pi^2 r_1}{2}, \tag{8}$$

$$c = \left(\pi R + \sqrt{(R_x + r_1)^2 + r_1^2}\right)^2 - \qquad (9)$$
$$(\pi R + \lambda)^2 + \pi^2 R r_1 - \left(\frac{\pi R}{2}\right)^2 + \sqrt{(R_x + r_q)^2 + r_1^2} \pi r_1.$$

To obtain the length of interaction, L, the perimeter length of a semi-circle is used to define the relationship between L and the minor and major radius, $r_1$ and $r_2$, respectively, as shown:

$$L(\theta_{actuator}) = \frac{\pi}{2}(r_1 + r_2) - \pi R \qquad (10)$$

assuming a constant width, w, as discussed above. However, this does not provide a sufficient representation of the final inflated soft actuator 14. The actuators 14 do not retain the same longitudinal cross-section dimensions when pressurized. Therefore, an adjusted effective width is required to better represent the behavior of the soft actuators 14:

$$w_1(\theta_{actuator}) = w_0 - 2R\left(1 - \frac{h_1(\theta_{actuator}) - 2R}{h - 2R}\right) \qquad (11)$$

where $w_1$ represents the adjusted effective width of the actuator 14 and $h_1$ represents the variable height. Utilizing (10) and (11) to measure the effective area of interaction, a bending angle of 90° degrees is used as the variable input into the equation below to calculate the theoretical torque (T) generated by the exosuit 10:

$$T(\theta_{actuator}) = PLL_F w_1 \qquad (12)$$

where P is the pressure input parameter and $L_F$ remains as defined in Eq. 1.

Figure 7:
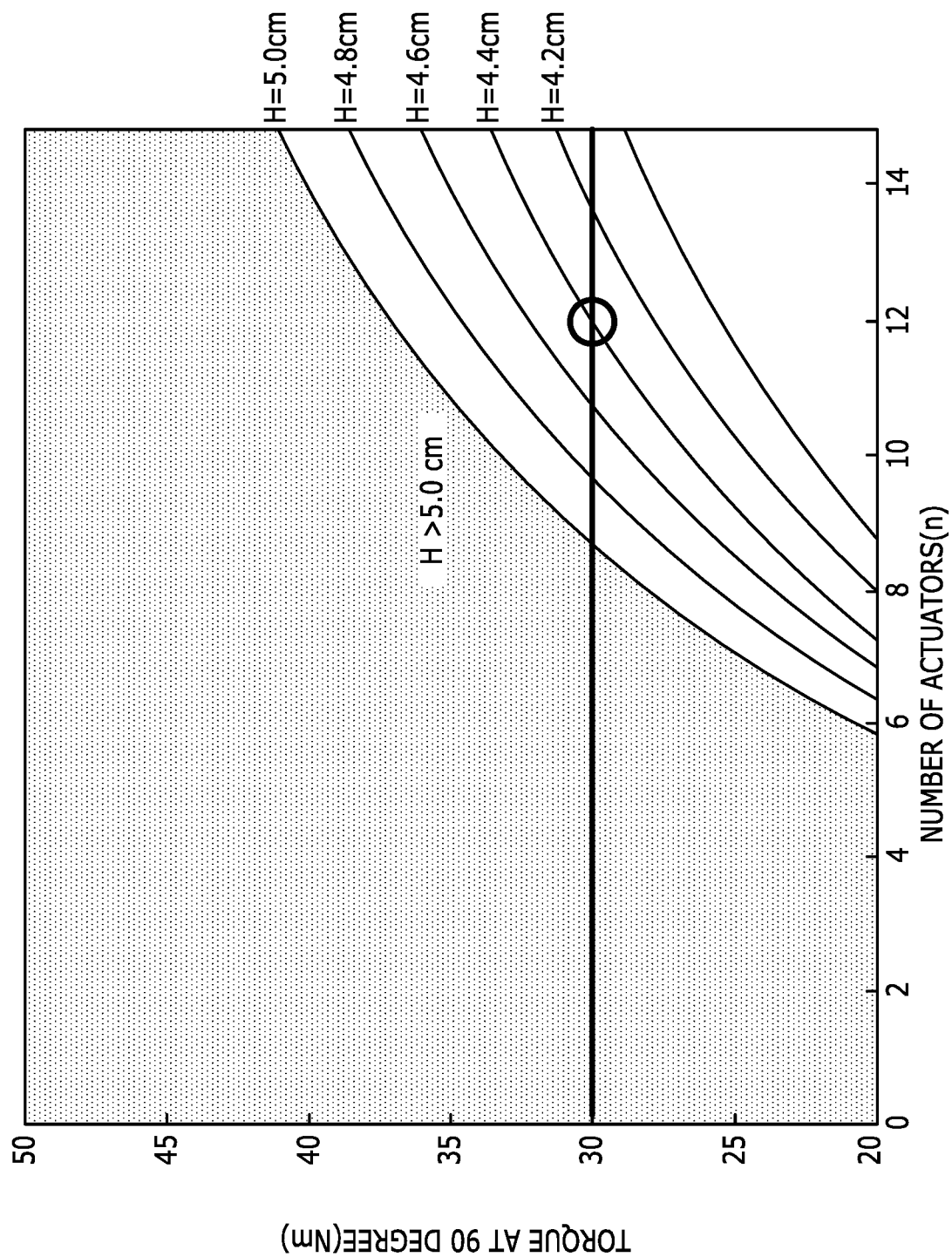
FIG. 7 illustrates various actuator heights (h) and quantities (n) plotted to assess potential solutions to finding optimum parameters that would yield 30 N·m of torque. The shaded regions indicated infeasible regions attributed to manufacturing constraints.

As shown in FIG. 7, the torque output of the array 22 is plotted against the number of individual actuators 14 for fixed h. An increasing soft actuator 14 radii R results in improved torque with diminishing returns from increasing the number n of actuators 14. Using the set 30 N·m as the minimum desired threshold and limiting the maximum pressure (e.g., to 275 kPa), multiple design parameters can be selected to generate a balance between manufacturability and ergonomics. In the illustrated embodiment, d=8 mm, number of actuators 14, n=12, and height of a deflated actuator 14, h=44 mm. The width of the actuator 14 is constrained to w=75 mm to fit the diameter of an average adult arm.

Figure 8A:
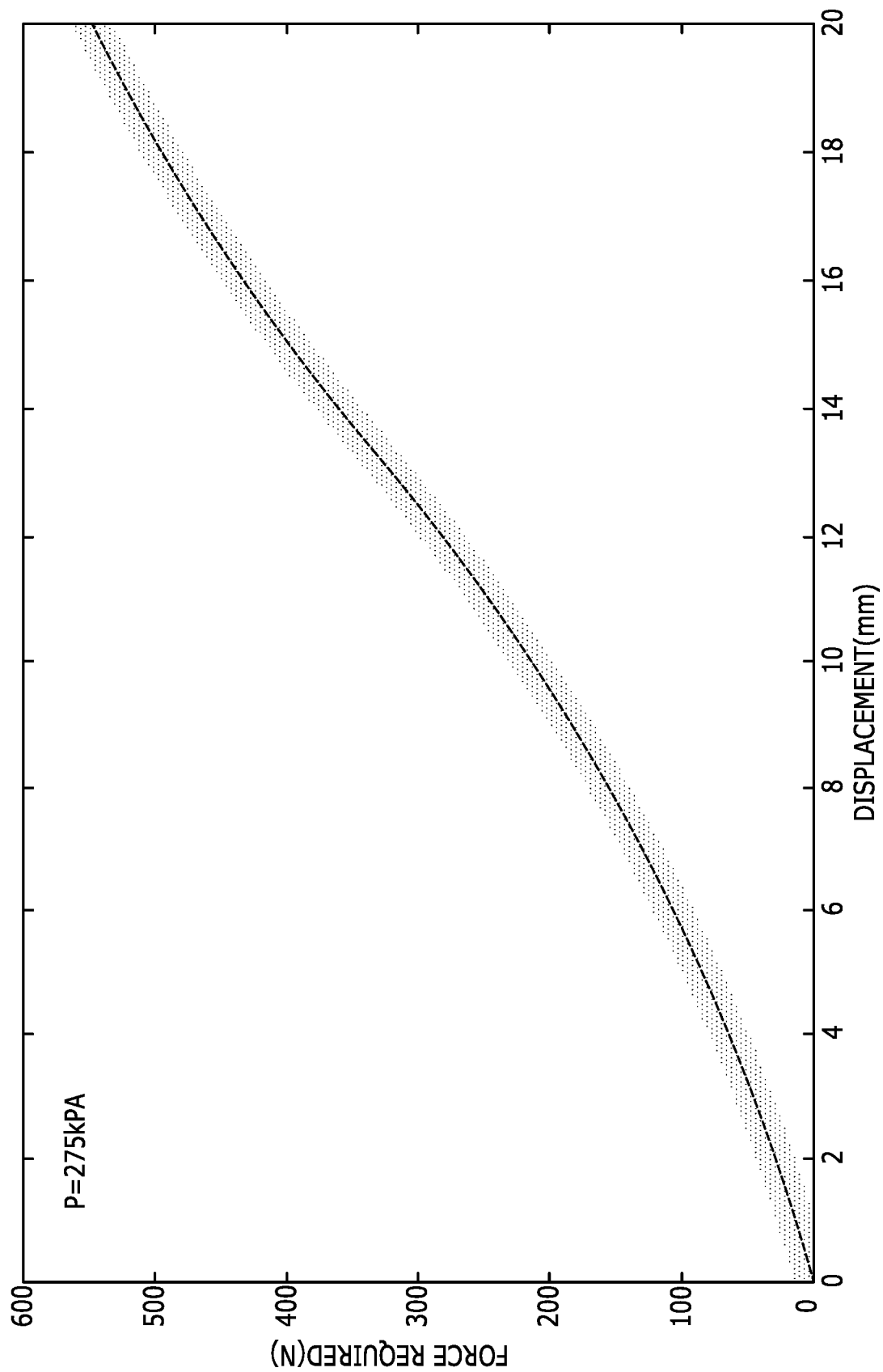
FIG. 8A illustrates a graph showing displacement of the actuator of FIG. 2A and the corresponding force required to cause displacement during testing of an individual actuator to determine stiffness when fully pressurized.
Figure 8B:
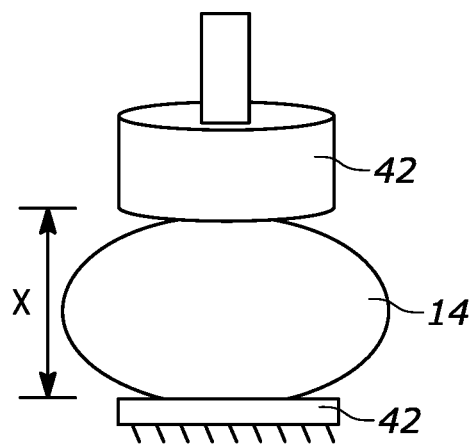
FIG. 8B illustrates an actuator of FIG. 2A in a universal tensile strength machine (UTM) before compression.
Figure 8C:
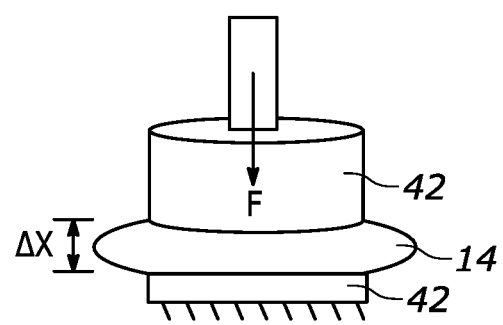
FIG. 8C illustrates an actuator of FIG. 2A in the UTM after compression.

As shown in FIGS. 8A-8C, a single soft actuator 14 was placed between compression platens 42 of a universal tensile strength machine (UTM) (e.g., Instron 5944, Instron Corp., High Wycombe, United Kingdom) to determine its stiffness. The soft actuator 14 was inflated up to a pressure of 275 kPa (as per the design parameters) and compressed to a total displacement Δx (e.g., 19.5 mm), to the spacing between two adjacent actuators 14. The pressure was held constant for the entirety of the test. A high force to weight ratio of 211.5 N/g was obtained, given a single actuator 14 weight of 2.6 g and a force output of 550N. A calculated stiffness of 28.2 kN/m was found as a result of the maximum displacement and force obtained.

Figure 9:
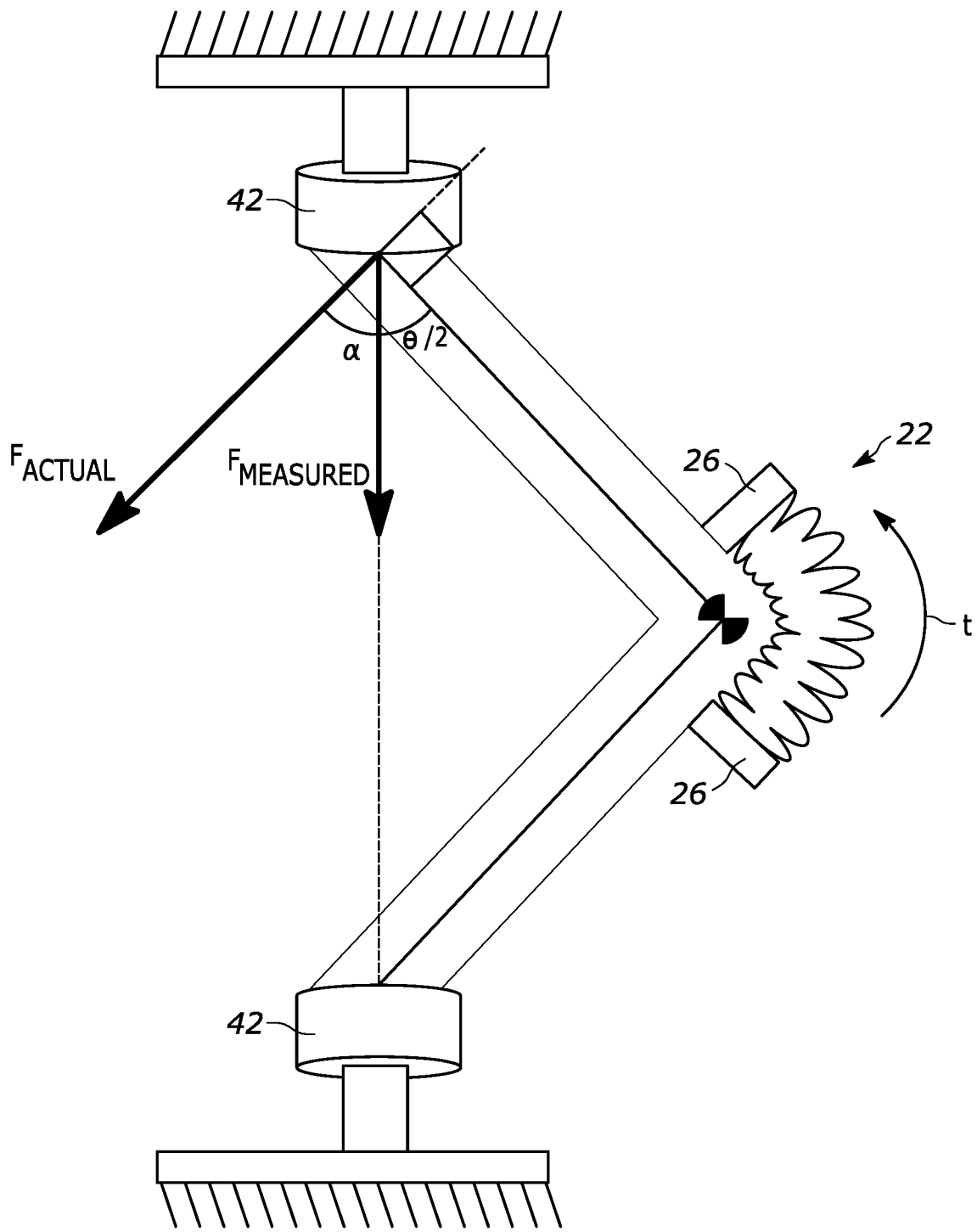
FIG. 9 illustrates a setup of torque test, showing the soft exosuit of FIG. 3A strapped to an analog joint while fixed in the UTM.
Figure 10:
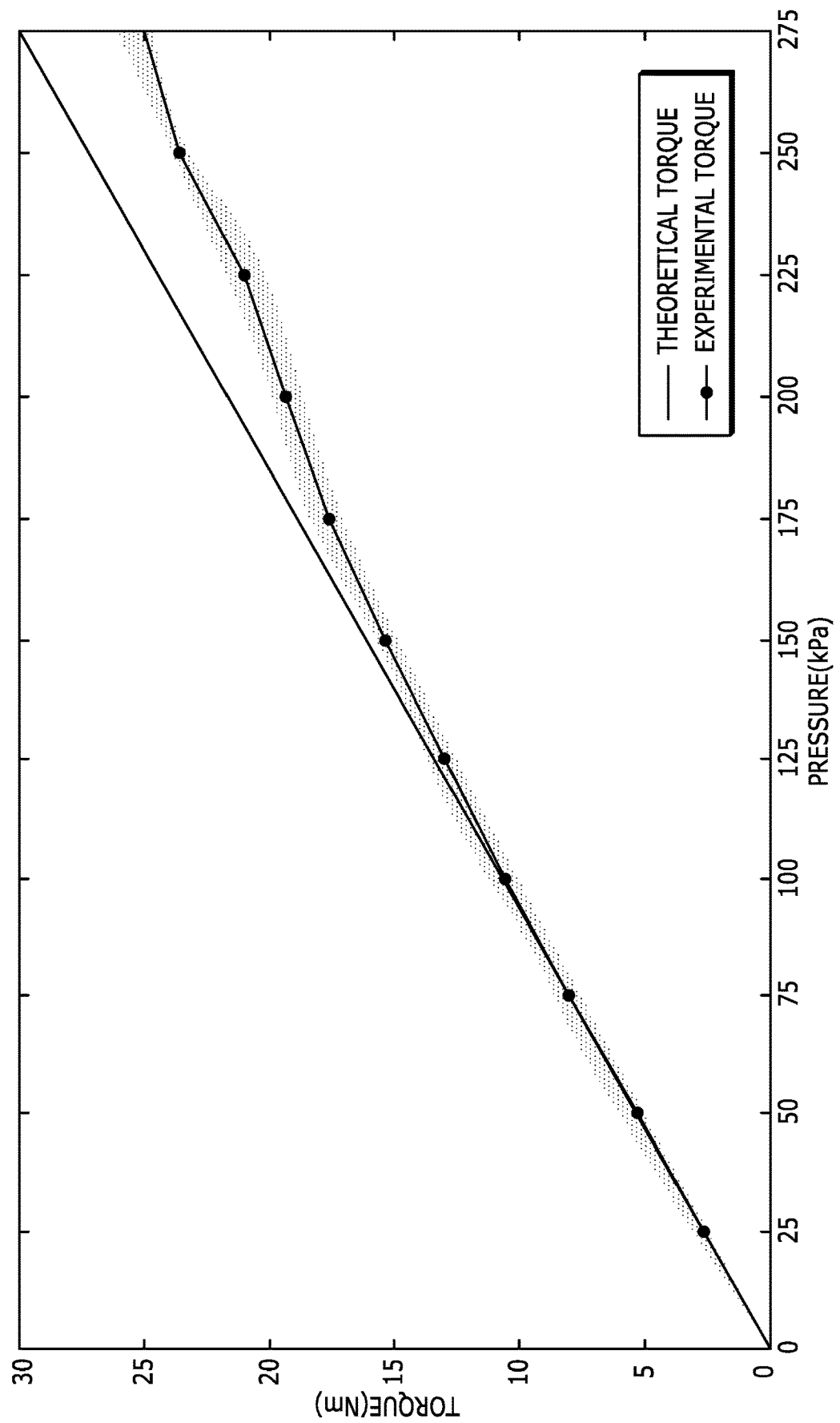
FIG. 10 graphically illustrates results of five trials for the torque test, displaying a linear relationship between the predicted torque values and the measured torque output of the soft exosuit of FIG. 3A.

To verify the torque output compared to the theoretical model shown in (12), the exosuit 10 was secured to an analog elbow joint and placed in a UTM, with the joint angle fixed at 90° (see e.g., FIG. 9). The actuator array was inflated in increments of 25 kPa up to a maximum of 275 kPa for five trials. As shown in FIG. 10, a linear trend was observed for the relationship between pressure and torque (r-squared of 0.99). The linear regression model was compared to the theoretical model, and an average error of approximately 6.6% was observed. Overall, a maximum experimental torque of 27.1±0.67 N·m at a fixed 90° angle and 275 kPa was obtained in contrast to the estimated 30 N·m, validating the accuracy of the model.

Figure 11B:
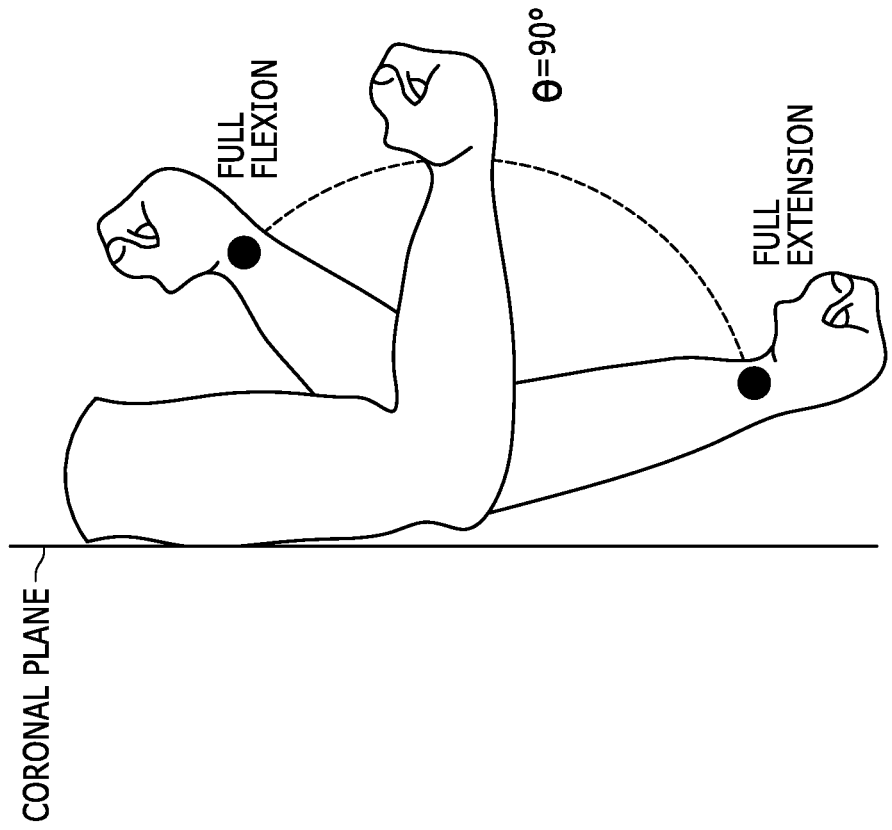
FIG. 11B illustrates measured positions of the arm for participant testing.
Figure 11A:
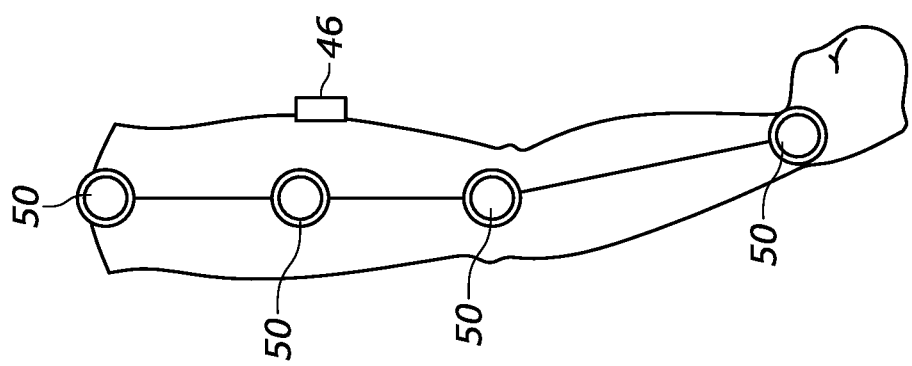
FIG. 11A illustrates a surface electromyography sensor and motion capture marker placement on a user's arm.

As shown in FIG. 11A, a surface electromyography (sEMG) sensor 46 was placed at a bicep of the participant, to measure muscle activity during test trials. The maximum voluntary contraction (MVC) and the muscle activity during relaxation was collected as per standard International Society of Electrophysiology and Kinesiology (ISEK) protocols. The MVC limit was measured with the participant exerting maximum force against the load cell 42 of the UTM with their elbow at a 90° bend, and their upper arm lying on the coronal plane (see e.g., FIG. 11B). Three individual tests were recorded, which result in an average maximum load of 73.6±9N (7.5±0.9 kg) of force exerted by the participant. This value was considered the maximum load the participant can support at 90°. In some embodiments, a control method of exosuit actuation is built on a single-input-single-output (SISO) open loop system. Pressure is manually defined and monitored by an adjustable analog pneumatic regulator.

The lifting assistance provided by the exosuit 10 was verified by repeating the procedure of flexing the arm from full extension to a fixed elbow joint angle position at 90° and holding the arm there for five seconds before relaxing back to full extension. The isometric contractions (i.e. muscle contractions while the arm does not move) of the bicep were monitored. Initially, a baseline for the isometric contraction of the participant's bicep was established by recording the sEMG activity while performing the procedure without load, with and without assistance from the exosuit 10 (see e.g., FIG. 11C). The same procedure was then repeated for varying load of 1.5 kg and 2.5 kg, first without then with assistance as shown in FIGS. 11D and E.

The sEMG data was normalized with respect to the MVC and shows the unassisted isometric contractions for the 1.5 kg load to be 19.2% of the participant's MVC, and 31.2% of the MVC for the 2.5 kg load. It was observed that the averaged exosuit 10 assistance provides 43% and 63% reduction in the activity of the bicep during the static test (see e.g., FIGS. 11D and 11E). The sEMG data in FIGS. 11D and 11E indicate that there is residual muscle activity present even when assistance is provided by the exosuit 10 possibly due to the effects of the participant straining to prevent unwanted wrist extension.

Figure 12:
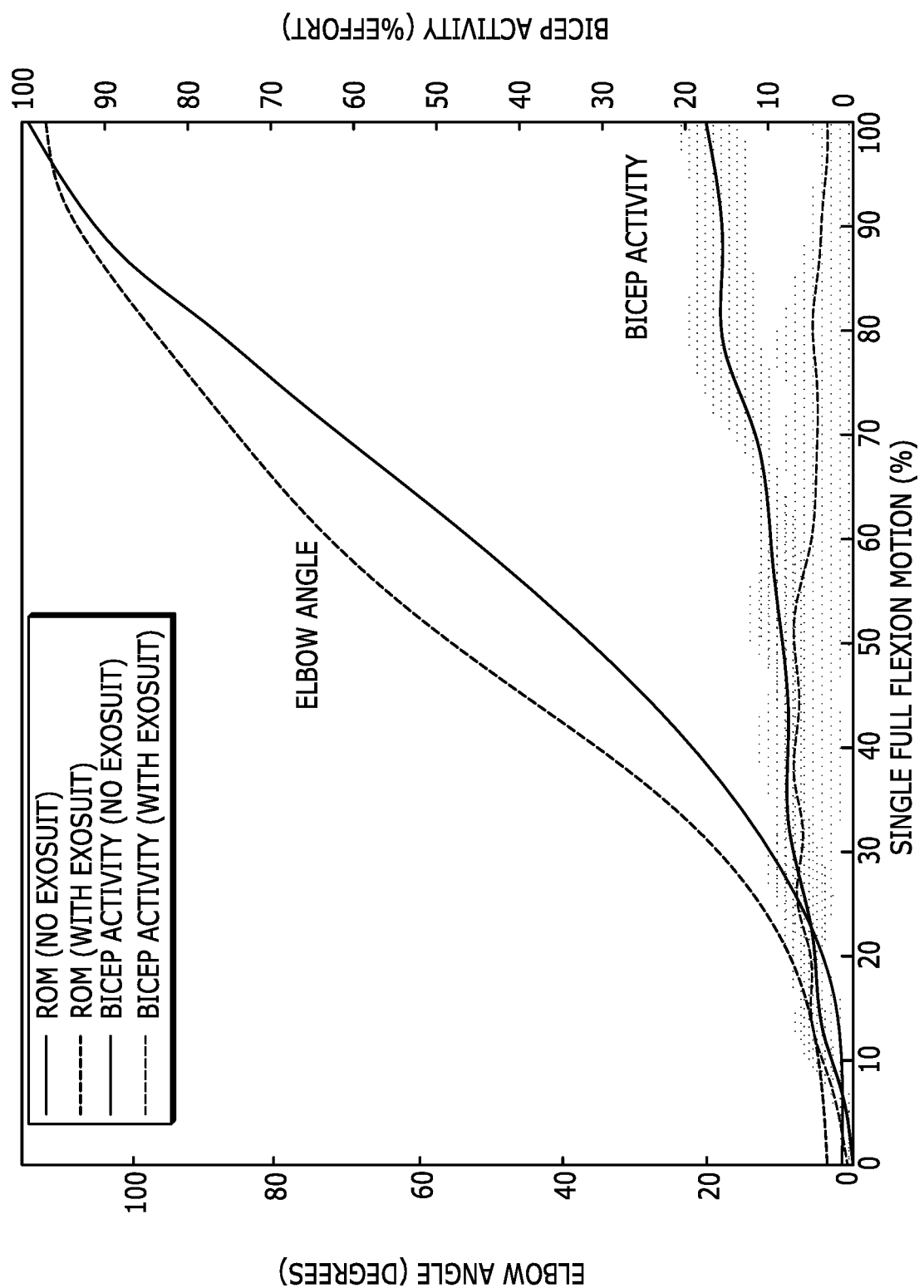
FIG. 12 graphically shows a range of motion of the participant with and without wearing the soft exosuit from 0° (full extension) to 115° (full flexion) shown on a vertical axis on the left. Surface electromyography (sEMG) data during motion is shown on the right.

A test was also performed to quantify whether the participant's ROM may be affected by the exosuit 10. The sEMG sensor 46 was used to monitor the concentric contractions (i.e. muscle contraction during arm motion) of the bicep from full extension to full flexion for signs of assistance through muscle activity reduction. Passive reflective markers 50 (see e.g., FIG. 11A) were placed at the top of the shoulder (acromion), center of upper arm (humerus), elbows axis of rotation (medial epicondyle), and wrist (styloid process) (see e.g., FIG. 11B) to allow the motion capture system to track the motion during a single bicep curl. The participant performed a single curl with no assistance from the exosuit 10, then repeated the motion relying on only the exosuit 10 to achieve full flexion. Three trials were recorded with the upper arm remaining parallel to the coronal plane throughout the experiment. The observed angle at the elbow joint and corresponding bicep activity is shown in FIG. 12.

The total elbow angle prior to wearing the exosuit 10 spanned 115°±4° from full extension to full flexion. The range of motion while wearing the exosuit 10 was found to be 107°±8°. This verifies that the exosuit 10 does not obstruct 93% of the ROM. Additionally, a reduction of 47% in the muscle activity of the bicep was observed throughout the entire motion when the exosuit 10 is assisting. This validates that the exosuit 10 is capable of providing active assistance to the bicep through the entire motion.

An analytical model governing the bending behavior of two consecutive actuators and torque generated by the exosuit 10 was developed, with test results showing less than 10% error from the theoretical model. An elbow joint torque value of 27.6 N·m was achieved at 275 kPa, which is comparable to the 30 N/m maximum set by OSHA requirements in the USA. Further testing with a healthy participant was performed using sEMG sensors 46 and a motion capture system to assess the capabilities of the exosuit 10 to provide active assistance to the bicep during isometric and concentric contractions. Measurable assistance to lifting was observed with minimal obstruction to the user's range of motion for all experiments.

Various features and advantages of certain embodiments are set forth in the following claims.

What is claimed is:

1. An assisted lifting device comprising:
    a sleeve configured to be worn around a user's arm proximate an elbow; and
    an array coupled to the sleeve, the array comprising
        a first retainer positioned on a first end of the array and a second retainer positioned on a second end of the array,
        a first actuator including a first base configured to extend at least partially around the user's arm, the first actuator positioned between the first retainer and the second retainer, and
        a second actuator including a second base configured to extend at least partially around the user's arm, the second actuator spaced apart from the first actuator and positioned between the first retainer and the second retainer,
        wherein the first actuator and the second actuator are configured to be spaced apart by a fixed distance when in a deflated position, and wherein the first actuator and the second actuator are configured to expand and contact each other at a contact point when in an inflated position.

2. The assisted lifting device of claim 1, wherein the sleeve further includes an adjustable strap configured to be adjusted by the user.

3. The assisted lifting device of claim 1, wherein the first actuator is made from sheets of thermoplastic polyurethane material.

4. The assisted lifting device of claim 1, wherein the first actuator is positioned adjacent to the first retainer.

5. The assisted lifting device of claim 1, wherein the first actuator and the second actuator are fluid actuators, and wherein the array is curved in the inflated position.

6. The assisted lifting device of claim 1, wherein the first base is formed from an inextensible fabric.

7. An assisted lifting device comprising:
    a single sleeve configured to be worn on an arm of a subject;
    a plurality of inflatable actuators coupled to the sleeve, wherein each of the actuators includes a base and a free end, and the plurality of actuators are moveable between a deflated position and an inflated position;
    wherein the bases of adjacent actuators are fixed a predetermined distance apart along the sleeve such that each of the plurality of actuators is spaced apart from one another in the deflated position, and wherein the free ends of adjacent actuators are configured to be spaced further apart than the predetermined distance in the inflated position causing the plurality of actuators to curve around the arm of the subject; and
    a triangular retainer coupled to the sleeve and the other one of the outermost actuators, the retainer configured to maintain the perpendicular orientation of the respective outermost actuators upon inflation of the plurality of actuators.

8. The assisted lifting device of claim 7, wherein the sleeve further includes an adjustable strap configured to be adjusted by the user in order to achieve a proper fit on the user's arm.

* * * * *